(12) United States Patent
Takami et al.

(10) Patent No.: US 10,456,188 B2
(45) Date of Patent: Oct. 29, 2019

(54) HEATING TREATMENT APPARATUS AND CONTROLLER OF THE SAME

(71) Applicant: OLYMPUS CORPORATION, Hachioji-shi, Tokyo (JP)

(72) Inventors: Sadayoshi Takami, Hachioji (JP); Yoshitaka Honda, Hachioji (JP); Takashi Irisawa, Hachioji (JP); Kazue Tanaka, Sagamihara (JP); Toshifumi Katsuragi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/497,363

(22) Filed: Apr. 26, 2017

(65) Prior Publication Data

US 2017/0224407 A1 Aug. 10, 2017

Related U.S. Application Data

(63) Continuation of application No. PCT/JP2016/063767, filed on May 9, 2016.

(30) Foreign Application Priority Data

Jul. 1, 2015 (JP) .................................. 2015-132785

(51) Int. Cl.
*A61B 18/10* (2006.01)
*A61B 18/08* (2006.01)
(Continued)

(52) U.S. Cl.
CPC .............. *A61B 18/10* (2013.01); *A61B 18/08* (2013.01); *A61B 18/085* (2013.01);
(Continued)

(58) Field of Classification Search
CPC ............ A61B 18/08–085; A61B 18/10; A61B 2018/00714; A61B 2018/00702; A61B 2018/00779
See application file for complete search history.

(56) References Cited

U.S. PATENT DOCUMENTS

| 5,443,463 A * | 8/1995 | Stern ....................... A61B 18/14 606/51 |
| 2002/0082593 A1* | 6/2002 | Hareyama ............ A61B 18/085 606/38 |

(Continued)

FOREIGN PATENT DOCUMENTS

| EP | 2415416 A1 | 2/2012 |
| JP | 2001-269352 A | 10/2001 |

(Continued)

OTHER PUBLICATIONS

Jul. 10, 2017 Written Opinion of the International Searching Authority issued in International Application No. PCT/JP2016/063767.

(Continued)

*Primary Examiner* — Jaymi E Della
*Assistant Examiner* — Sean W Collins
(74) *Attorney, Agent, or Firm* — Oliff PLC

(57) ABSTRACT

A heating treatment apparatus to treat a living tissue by heating the living tissue includes a first holding member and a second holding member, a first heat generating element provided on the first holding member, a second heat generating element provided on the second holding member, a power supply unit supplying electric power to cause the first heat generating element and the second heat generating element to generate heat, and a control unit controlling operations of the power supply unit. The control unit switches a mode between a first mode and a second mode during treatment of the living tissue. Temperatures of the first heat generating element and the second heat generating (Continued)

element are controlled to the same temperature in the first mode and to different temperatures in the second mode.

21 Claims, 12 Drawing Sheets

(51) Int. Cl.
   *A61B 18/12* (2006.01)
   *A61B 18/14* (2006.01)
   *A61B 18/00* (2006.01)

(52) U.S. Cl.
   CPC ...... *A61B 18/1206* (2013.01); *A61B 18/1442* (2013.01); *A61B 2018/0063* (2013.01); *A61B 2018/00589* (2013.01); *A61B 2018/00601* (2013.01); *A61B 2018/00654* (2013.01); *A61B 2018/00702* (2013.01); *A61B 2018/00714* (2013.01); *A61B 2018/00797* (2013.01); *A61B 2018/00875* (2013.01)

(56) References Cited

U.S. PATENT DOCUMENTS

| | | | | |
|---|---|---|---|---|
| 2003/0171747 | A1* | 9/2003 | Kanehira | A61B 17/3201 606/45 |
| 2006/0217706 | A1* | 9/2006 | Lau | A61B 17/29 606/45 |
| 2011/0077631 | A1* | 3/2011 | Keller | A61B 18/1206 606/33 |
| 2012/0022517 | A1* | 1/2012 | Stuebe | A61B 18/085 606/31 |
| 2012/0059372 | A1* | 3/2012 | Johnson | A61B 18/1445 606/45 |
| 2013/0338665 | A1* | 12/2013 | Tanaka | A61B 18/085 606/41 |
| 2015/0223868 | A1* | 8/2015 | Brandt | A61B 18/1445 606/40 |

FOREIGN PATENT DOCUMENTS

| | | |
|---|---|---|
| JP | 2007-037845 A | 2/2007 |
| JP | 2012-125338 A | 7/2012 |
| JP | 2014-008136 A | 1/2014 |

OTHER PUBLICATIONS

Jul. 12, 2016 Search Report issued in International Patent Application No. PCT/JP2016/063767.
Jan. 11, 2018 International Preliminary Report on Patentability issued in International Patent Application No. PCT/JP2016/063767.
Jun. 27, 2018 Extended European Search Report issued in European Patent Application No. 16817558.6.
Dec. 17, 2018 Office Action issued in European Patent Application No. 16817558.6.
Feb. 1, 2019 Office Action issued in Chinese Patent Application No. 201680003478.7.

* cited by examiner

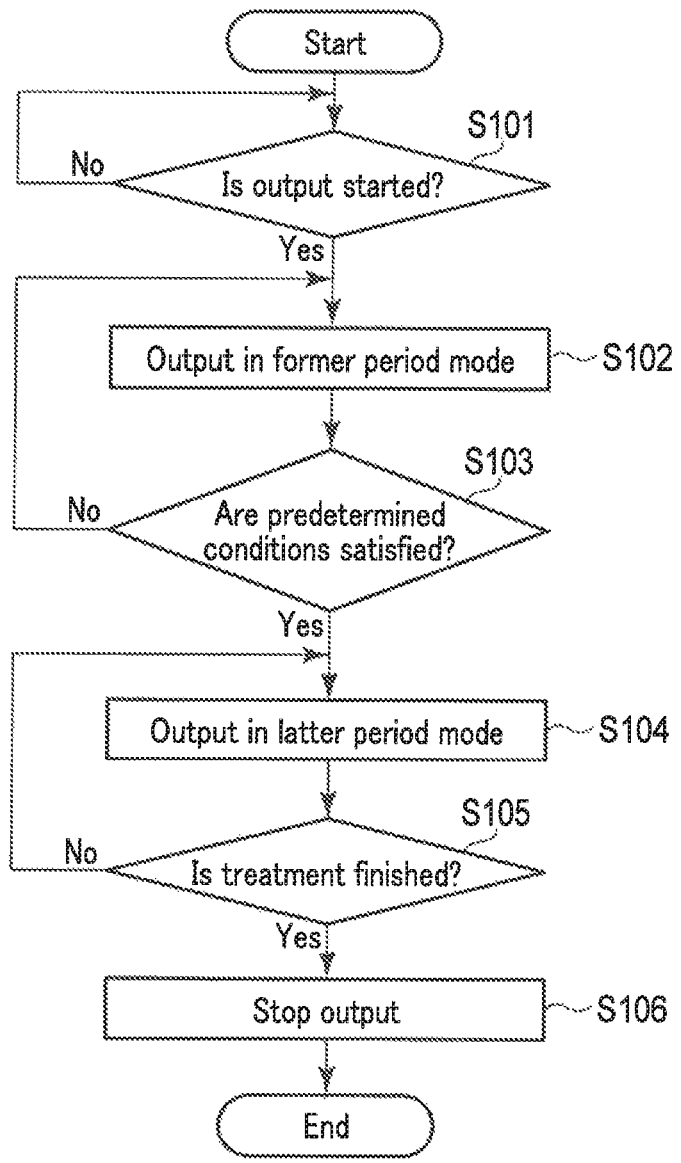
F I G. 4

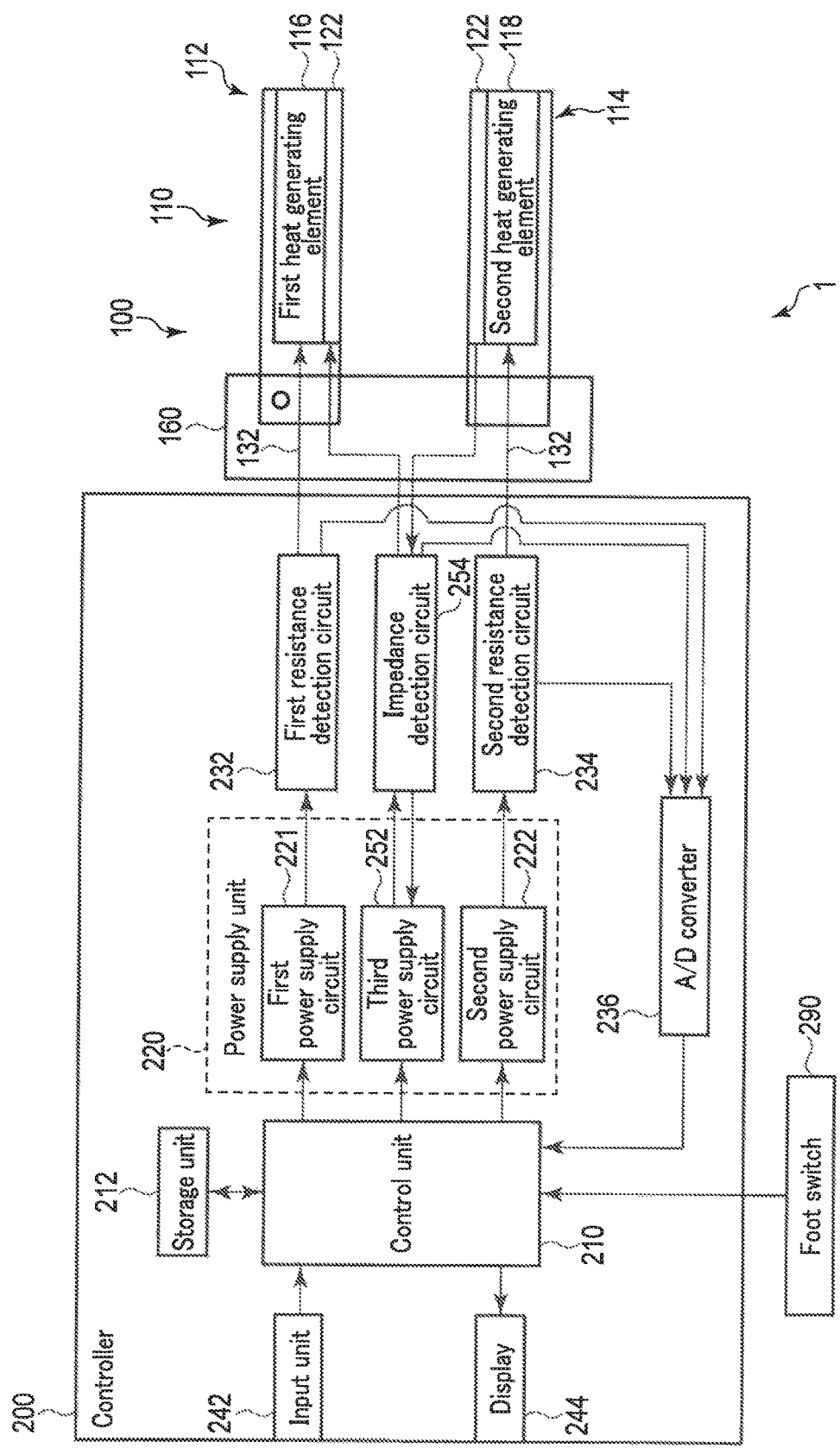
F I G. 13

HEATING TREATMENT APPARATUS AND CONTROLLER OF THE SAME

CROSS-REFERENCE TO RELATED APPLICATIONS

This application is a Continuation application of PCT Application No. PCT/JP2016/063767, filed May 9, 2016 and based upon and claiming the benefit of priority from prior Japanese Patent Application No. 2015-132785, filed Jul. 1, 2015, the entire contents of all of which are incorporated herein by reference.

BACKGROUND OF THE INVENTION

1. Field of the Invention

The present invention relates to a heating treatment apparatus and a controller of the same.

2. Description of the Related Art

Generally, treatment apparatuses to hold a living tissue and treat the living tissue by heating the living tissue are known. For example, Japanese Patent Application KOKAI Publication No. 2014-8136 discloses a technique relating to a treatment apparatus capable of applying a high-frequency voltage to a held living tissue, heating the tissue with a heater, and cutting the living tissue with a cutter. In the treatment apparatus, when a pair of holding members holding a living tissue is heated with the heater, the holding members are adjusted to the same target temperature. Japanese Patent Application KOKAI Publication No. 2014-8136 discloses an efficient method in such temperature adjustment.

BRIEF SUMMARY OF THE INVENTION

According to an aspect of the invention, a heating treatment apparatus to treat a living tissue by heating the living tissue includes a first holding member, a second holding member configured to hold the living tissue together with the first holding member, a first heat generating element provided on the first holding member and configured to heat the first holding member to heat the living tissue, a second heat generating element provided on the second holding member and configured to heat the second holding member to heat the living tissue, a power supply unit which supplies electric power to cause the first heat generating element and the second heat generating element to generate heat, and a control unit which controls operations of the power supply unit, and switching a mode between a first mode and a second mode during treatment of the living tissue, the first mode being a mode to perform control to set the first heat generating element and the second heat generating element to an equal temperature, the second mode being a mode to perform control to set the first heat generating element and the second heat generating element to different temperatures.

According to an aspect of the invention, a controller of a heating treatment apparatus to perform treatment by holding and heating a living tissue with a first holding member provided with a first heat generating element and a second holding member provided with a second heat generating element includes a power supply unit which supplies electric power to cause the first heat generating element and the second heat generating element to generate heat, and a control unit which controls operations of the power supply unit, and switching a mode between a first mode and a second mode during treatment of the living tissue, the first mode being a mode to perform control to set the first heat generating element and the second heat generating element to an equal temperature, the second mode being a mode to perform control to set the first heat generating element and the second heat generating element to different temperatures.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a flowchart illustrating an outline of an example of operations of the heating treatment apparatus according to an embodiment;

FIG. 13 is a block diagram illustrating a schematic configuration example of a heating treatment apparatus according to a second embodiment.

DETAILED DESCRIPTION OF THE INVENTION

First Embodiment

Figure 1:
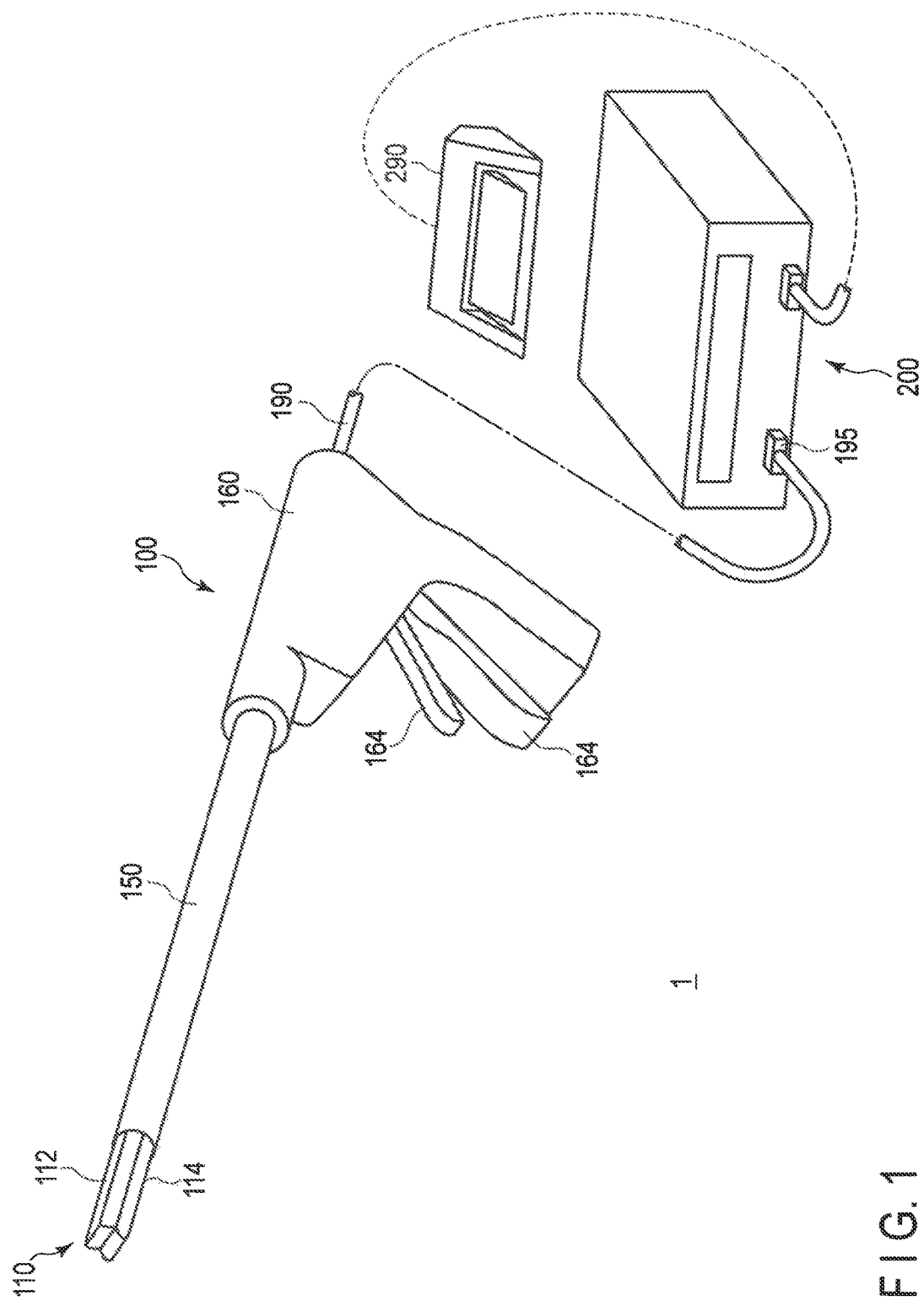
FIG. 1 is a diagram illustrating a schematic configuration example of a heating treatment apparatus according to an embodiment.

A first embodiment of the present invention will be explained hereinafter with reference to drawings. FIG. 1 shows a schematic diagram of an external appearance of a medical heating treatment apparatus 1 according to the present embodiment. The heating treatment apparatus 1 is an apparatus used for treatment of a living tissue, and used for, for example, treatment to seal, dissect, and/or incise the blood vessels and/or intestinal tracts. The heating treatment apparatus 1 performs treatment by applying thermal energy on the living tissue. As shown in FIG. 1, the heating treatment apparatus 1 includes a treatment tool 100 and a controller 200.

The treatment tool 100 is a linear-type treatment tool for surgical treatment to pierce, for example, the abdominal wall to perform treatment. The treatment tool 100 includes a handle 160, a shaft 150 attached to the handle 160, and a holding unit 110 provided at a distal end of the shaft 150.

The holding unit 110 includes a first holding member 112 and a second holding member 114. The holding unit 110 is opened and closed by displacing the first holding member 112 with respect to the second holding member 114. The holding unit 110 is configured to hold a living tissue serving as treatment target between the first holding member 112 and the second holding member 114. The holding unit 110 serves as a treatment unit to hold the living tissue serving as the treatment target and perform treatment, such as coagulation and incision of the living tissue. In the following explanation, the holding unit 110 side in the treatment tool 100 will be referred to as distal end side, and the handle 160 side will be referred to as proximal end side. The handle 160 includes a plurality of operating knobs 164 to operate the holding unit 110.

The shape of the treatment tool 100 explained herein is an example as a matter of course, and may be another shape as long as the treatment tool 100 has a similar function. For example, the shaft may be curved. In addition, the technique according to the present embodiment is not limited to a treatment apparatus used for rigid scope surgery as shown in FIG. 1, but may be applied to a treatment apparatus used for endoscope surgery using a flexible endoscope.

The treatment tool 100 is connected with the controller 200 via a cable 190. The cable 190 and the controller 200 are connected via a connector 195, and this connection is detachable. Specifically, the heating treatment apparatus 1 is configured to enable exchange of the treatment tool 100 for each treatment.

The controller 200 is connected with a foot switch 290. The foot switch 290 operated by foot may be replaced by a switch operated by hand or another switch. Turning on/off of supply of energy from the controller 200 to the treatment tool 100 is switched by operator's operating a pedal of the foot switch 290.

Figure 2:
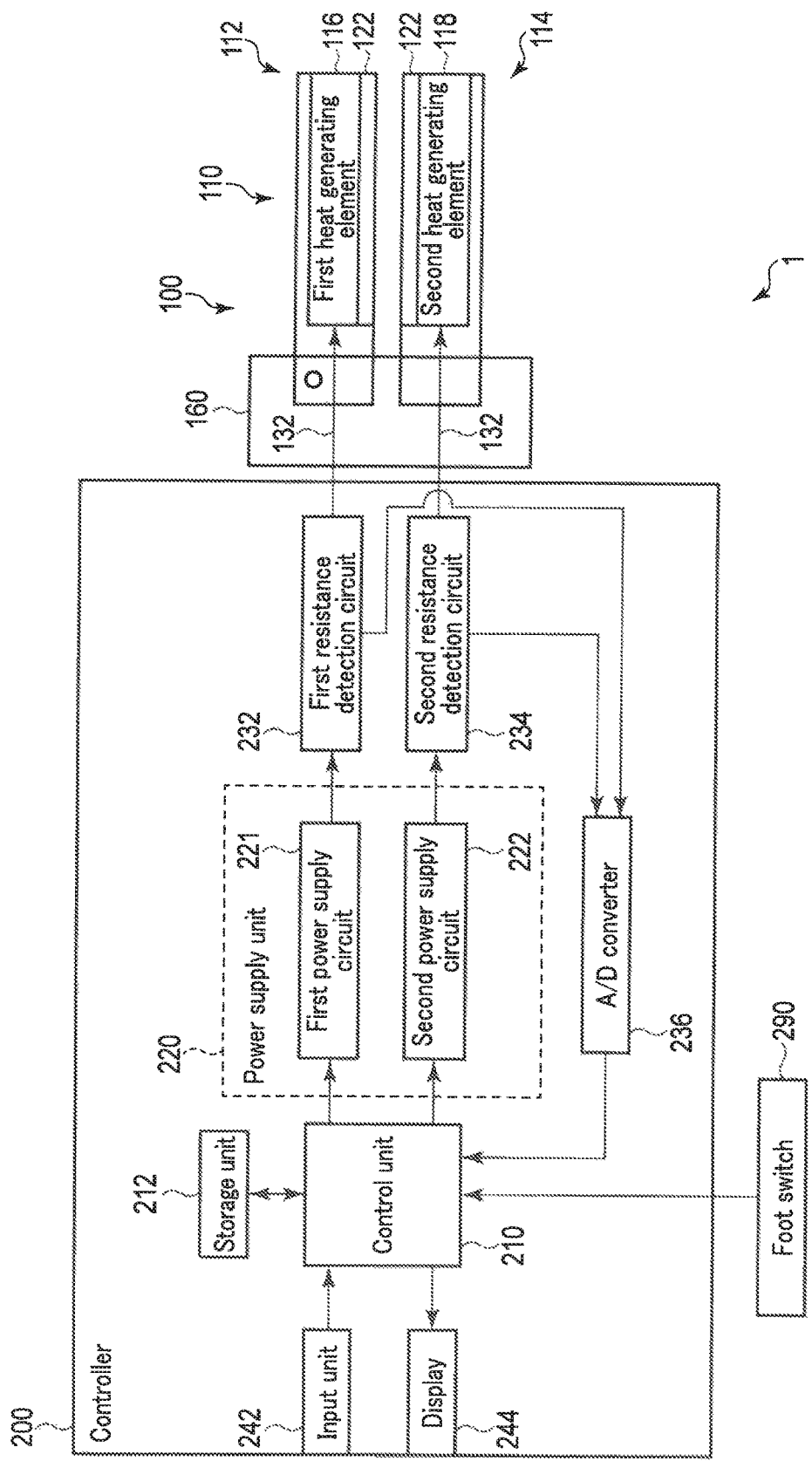
FIG. 2 is a block diagram illustrating a schematic configuration example of a heating treatment apparatus according to a first embodiment.

The configuration example of the heating treatment apparatus 1 will be further explained hereinafter, with reference to the schematic diagram shown in FIG. 2. The first holding member 112 and the second holding member 114 have the same structure. Specifically, each of the first holding member 112 and the second holding member 114 has a heat transfer member 122. The heat transfer member 122 is formed of metal with high thermal conductivity, such as copper. The heat transfer member 122 of the first holding member 112 and the heat transfer member 122 of the second holding member 114 are provided to be opposed to each other. Specifically, each heat transfer member 122 is provided to contact the living tissue.

The heat transfer member 122 of the first holding member 112 is provided with a first heat generating element 116. In the same manner, the heat transfer member 122 of the second holding member 114 is provided with a second heat generating element 118. Each of the first heat generating element 116 and the second heat generating element 118 includes a heater.

Figure 3:
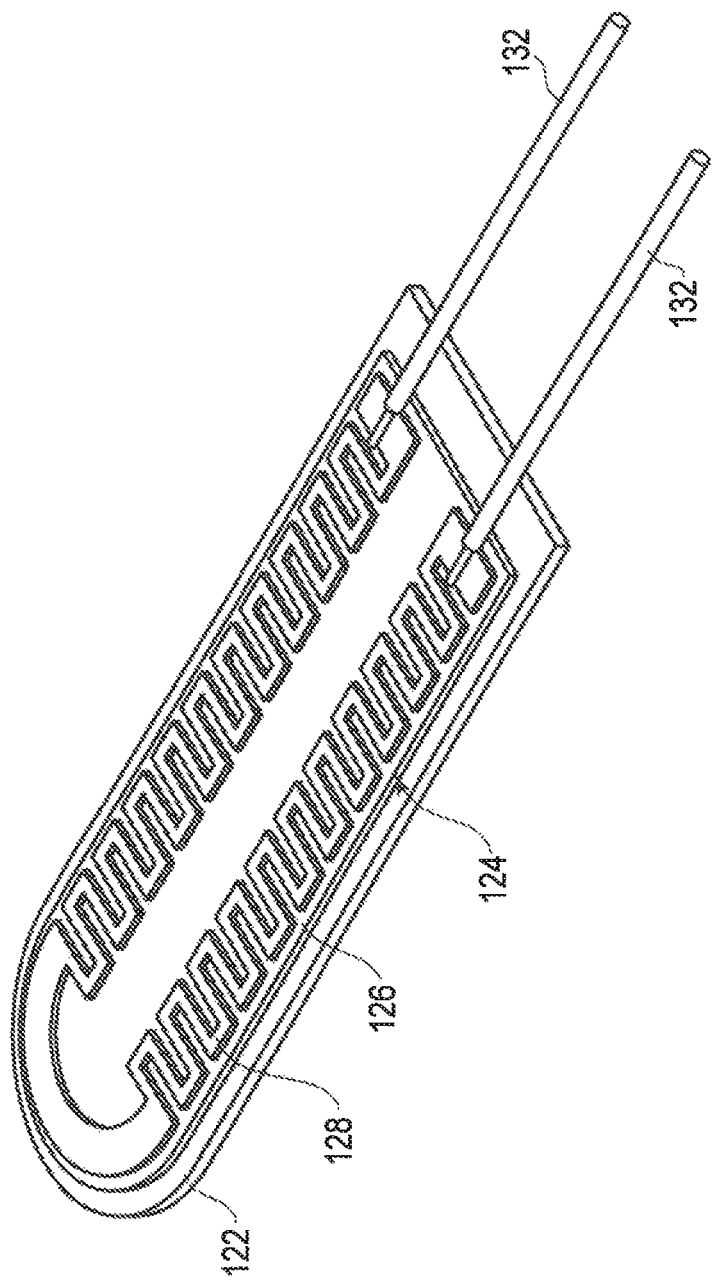
FIG. 3 is a perspective view illustrating a schematic configuration example of a heater of the heating treatment apparatus according to an embodiment.

The heat transfer member 122 and the heater 124 will be further explained with reference to FIG. 3. As shown in FIG. 3, the heater 124 has a structure in which a heat generating member 128 is provided on a substrate 126. The substrate 126 is, for example, a polyimide substrate. The substrate 126 has a size smaller than the heat transfer member 122, and has a shape similar to the heat transfer member 122. The heat generating member 128 is, for example, a stainless steel (SUS) resistance pattern formed on the substrate 126. The heat generating member 128 has both ends provided on the proximal end side, and has a pattern having a substantially U shape. This pattern has a thin line width to increase an electrical resistance value, and has a wave shape to cover a large area of the substrate. End portions of the heat generating member 128 are connected with respective one ends of lead wires 132.

The other end of each lead wire 132 is electrically connected with the controller 200. When electric power is supplied to the heat generating member 128, the heat generating member 128 generates heat. The heat generated with the heat generating member 128 is transferred to the heat transfer member 122 through the substrate 126. The heat is transferred to the living tissue contacting the heat transfer member 122, and the living tissue is treated by heating.

With reference to FIG. 2 again, the controller 200 will be explained hereinafter. The controller 200 includes a control unit 210 and a storage unit 212. The control unit 210 controls operations of the units of the controller 200. The control unit 210 includes a Central Processing Unit (CPU), an Application Specific Integrated Circuit (ASIC), or a Field Programmable Gate Array (FPGA), or the like. The control unit 210 may be formed of a CPU, or may be formed of a plurality of CPUs. Operations of the control unit 210 are performed in accordance with programs stored in the storage unit 212 and the control unit 210, for example. The storage unit 212 stores various pieces of information used for processing of the control unit 210. The storage unit 212 also stores programs of processing performed in the control unit 210.

The controller 200 includes a power supply unit 220 including a first power supply circuit 221 and a second power supply circuit 222. The first power supply circuit 221 is a circuit outputting electric power to be supplied to the first heat generating element 116. The second power supply circuit 222 is a circuit outputting electric power to be supplied to the second heat generating element 118. Each of the first power supply circuit 221 and the second power supply circuit 222 is connected with the control unit 210, and outputs electric power under the control of the control unit 210.

The controller 200 also includes a first resistance detection circuit 232, a second resistance detection circuit 234, and an A/D converter 236. The first resistance detection circuit 232 is inserted into a circuit connecting the first power supply circuit 221 with the first heat generating element 116, and outputs an analog signal corresponding to a resistance value of the first heat generating element 116. In the same manner, the second resistance detection circuit 234 is inserted into a circuit connecting the second power supply circuit 222 with the second heat generating element 118, and outputs an analog signal corresponding to a resistance value of the second heat generating element 118. The first resistance detection circuit 232 and the second resistance detection circuit 234 are connected with the A/D converter 236. Signals output from the first resistance detection circuit 232 and the second resistance detection circuit 234 are transmitted to the A/D converter 236. The A/D converter 236 converts the analog signal input from the first resistance detection circuit 232 and the second resistance detection circuit 234 into digital signals, and transmits the digital signals to the control unit 210. As described above, the control unit 210 acquires information relating to resistance values of the first heat generating element 116 and the second heat generating element 118.

The resistance values of the first heat generating element 116 and the second heat generating element 118 change according to respective temperatures of the first heat generating element 116 and the second heat generating element 118. Accordingly, the temperatures of the first heat generating element 116 and the second heat generating element 118 can be acquired based on these resistance values. The control unit 210 acquires information of the temperatures of the first heat generating element 116 and the second heat generating element 118, based on information relating to the resistance values.

The controller 200 includes an input unit 242 and a display 244. The input unit 242 is a unit receiving user's instructions. The input unit 242 includes, for example, any of ordinary input devices, such as a button switch, a slider, a dial, a keyboard, and a touch panel. The input unit 242 transmits user's instructions to the control unit 210. In the same manner, the foot switch 290 is also connected with the control unit 210.

The display 244 is a unit displaying various pieces of information relating to the controller 200. The display 244 includes, for example, any of display devices, such as a display panel using a LED. The display 244 is connected with the control unit 210.

The following is explanation of operations of the heating treatment apparatus 1 according to the present embodiment. The heating treatment apparatus 1 according to the present embodiment operates, first, in a former period mode to control the first heat generating element 116 and the second heat generating element 118 to respective predetermined target temperatures. Thereafter, when predetermined conditions are satisfied, the heating treatment apparatus 1 operates in a latter period mode to control the first heat generating element 116 and the second heat generating element 118 to respective predetermined target temperatures different from those of the former period mode. The details of the former period mode and the latter period mode will be described later. In addition, the details of predetermined conditions to switch the mode from the former period mode to the latter period mode will be described later. The outline of operations of the heating treatment apparatus 1 will be explained with reference to the flowchart shown in FIG. 4.

At Step S101, the control unit 210 determines whether to start output. For example, when the foot switch 290 is turned on, it is determined to start output. When output is not started, the process repeats Step S101, and waits. By contrast, when output is started, the process goes to Step S102.

At Step S102, the control unit 210 performs output control in the former period mode. At this step, the control unit 210 calculates temperatures of the first heat generating element 116 and the second heat generating element 118, based on the resistance values of the first heat generating element 116 and the second heat generating element 118 acquired using the first resistance detection circuit 232 and the second resistance detection circuit 234. The control unit 210 calculates an optimal output power to set the temperature of the first heat generating element 116 to a target temperature of the first heat generating element 116 in the former period mode, based on the current temperature of the first heat generating element 116. The control unit 210 causes the first power supply circuit 221 to output the calculated power. In the same manner, the control unit 210 calculates an optimal output power to set the temperature of the second heat generating element 118 to a target temperature of the second heat generating element 118 in the former period mode, based on the current temperature of the second heat generating element 118. The control unit 210 causes the second power supply circuit 222 to output the calculated power. As described above, the temperatures of the first heat generating element 116 and the second heat generating element 118 are feedback-controlled by the control unit 210. By controlling the temperatures of the first heat generating element 116 and the second heat generating element 118, the temperatures of the respective heat transfer members 122 of the first holding member 112 and the second holding member 114 contacting the living tissue serving as the treatment target are controlled in the former period mode.

At Step S103, the control unit 210 determines whether predetermined conditions to switch from the former period mode to the latter period mode are satisfied. When predetermined conditions are not satisfied, the process returns to Step S102. Specifically, temperature control in the former period mode is continued. By contrast, when the predetermined conditions are satisfied, the process goes to Step S104.

At Step S104, the control unit 210 performs output control in the latter period mode. At this step, the control unit 210 calculates the temperatures of the first heat generating element 116 and the second heat generating element 118, based on the resistance values of the first heat generating element 116 and the second heat generating element 118 acquired using the first resistance detection circuit 232 and the second resistance detection circuit 234. The control unit 210 calculates an optimal output power to set the temperature of the first heat generating element 116 to a target temperature of the first heat generating element 116 in the latter period mode, based on the current temperature of the first heat generating element 116. The control unit 210 causes the first power supply circuit 221 to output the calculated power. In the same manner, the control unit 210 calculates an optimal output power to set the temperature of the second heat generating element 118 to a target temperature of the second heat generating element 118 in the latter period mode, based on the current temperature of the second heat generating element 118. The control unit 210 causes the second power supply circuit 222 to output the calculated power. As described above, the temperatures of the respective heat transfer members 122 of the first holding member 112 and the second holding member 114 contacting the living tissue serving as the treatment target are controlled in the latter period mode.

At Step S105, the control unit 210 determines whether the treatment is finished. Specifically, the control unit 210 determines whether predetermined conditions to stop the output in the latter period mode, for example, are satisfied. When the foot switch 290 is turned off, it is determined that the treatment is finished. When the treatment is not finished, the process returns to Step S104. Specifically, temperature control in the latter period mode is continued. By contrast, when the treatment is finished, the process goes to Step S106.

At Step S106, the control unit 210 causes the first power supply circuit 221 and the second power supply circuit 222 to stop output of the power. The process is finished by the above.

The following is explanation of the former period mode and the latter period mode. In the present embodiment, one of a first mode and a second mode is selected as the former period mode, and the other of the first mode and the second mode is selected as the latter period mode. The first mode is a mode in which the target temperature of the first heat generating element 116 is equal to the target temperature of the second heat generating element 118. By contrast, the second mode is a mode in which the target temperature of the first heat generating element 116 is different from the target temperature of the second heat generating element 118. Specifically, the present embodiment has the configuration in which, during the treatment, the state in which the target temperature of the first heat generating element 116 is equal to the target temperature of the second heat generating element 118 is switched to the state in which the target temperature of the first heat generating element 116 is different from the target temperature of the second heat generating element 118, or the state in which the target temperature of the first heat generating element 116 is different from the target temperature of the second heat generating element 118 is switched to the state in which the target temperature of the first heat generating element 116 is equal to the target temperature of the second heat generating element 118.

<Examples of Combinations of Former Period Mode and Latter Period Mode>

The following is examples of combinations of the former period mode and the latter period mode, and examples of conditions for switching from the former period mode to the latter period mode.

First Example

The first example explains the case where the former period mode is the first mode in which the target temperature of the first heat generating element 116 is equal to the target temperature of the second heat generating element 118, and the latter period mode is the second mode in which the target temperature of the first heat generating element 116 is different from the target temperature of the second heat generating element 118. More specifically, for example, in the former period mode, the target temperatures of the first heat generating element 116 and the second heat generating element 118 set to an optimal temperature for sealing the living tissue. For example, the optimal temperature for sealing the living tissue is within the range of 50° C. to 250° C., preferably 200° C. This example explains the case where the target temperature of the first heat generating element 116 and the second heat generating element 118 is 200° C. in the former period mode. In the latter period mode, the target temperature of the first heat generating element 116 is set to an optimal temperature for incising the living tissue, and the target temperature of the second heat generating element 118 is set to an optimal temperature for sealing the living tissue. An optimal temperature for incising the living tissue is within a range of 250° C. to 300° C., preferably 300° C. The optimal temperature for sealing the living tissue is as described above. The present example explains the case where the target temperature of the first heat generating element 116 is set to 300° C., and the target temperature of the second heat generating element 118 is set to 200° C., in the latter period mode.

Setting the treatment temperature to 200° C. that is relatively low enables deliberate sealing of the living tissue serving as the treatment target. Specifically, the living tissue is sealed, with the first heat generating element 116 and the second heat generating element 118 set to 200° C. in the former period mode.

By contrast, setting the treatment temperature to 300° C. that is relatively high enables incision of the living tissue serving as the treatment target, by burning off the living tissue. However, when both the first heat generating element 116 and the second heat generating element 118 are set to 300° C., the living tissue may be carbonized. For this reason, in the latter period mode of the first example, the first heat generating element 116 is set to 300° C., and the second heat generating element 118 is set to 200° C. In this manner, proper incision is expected without carbonization of the tissue. As described above, in the first example, the tissue is deliberately coagulated in the former period mode, and thereafter the tissue is slowly incised in the latter period mode.

Figure 5:
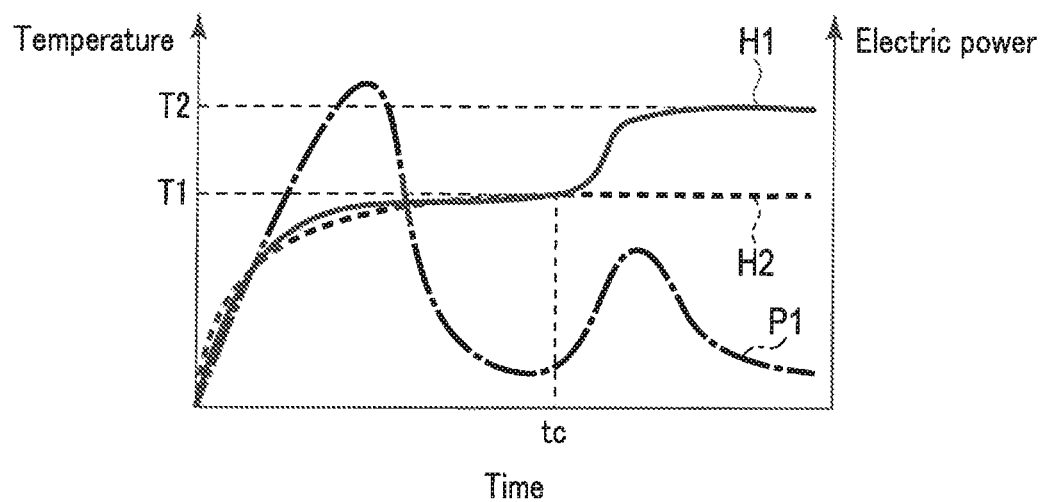
FIG. 5 is a diagram illustrating an example of outlines of a temperature and input power of a heat generating element according to a first example of a combination of a former period mode and a latter period mode.

FIG. 5 shows relation between the temperatures of the first heat generating element 116 and the second heat generating element 118, and the electric power input to the first heat generating element 116, with respect to the time during treatment. In FIG. 5, a solid line H1 indicates the temperature of the first heat generating element 116, a broken line H2 indicates the temperature of the second heat generating element 118, and a dashed line P1 indicates the electric power input to the first heat generating element 116. At time tc, the mode is switched from the first mode to the second mode. The temperature T1 is the target temperature of the first heat generating element 116 and the second heat generating element 118 in the former period mode. The temperature T1 is also the target temperature of the second heat generating element 118 in the latter period mode. The temperature T2 is the target temperature of the first heat generating element 116 in the latter period mode.

As shown in FIG. 5, before the time tc, because the electric power to be supplied to the first heat generating element 116 and the second heat generating element 118 is controlled in the first mode, the temperatures of the first heat generating element 116 and the second heat generating element 118 change in substantially the same manner. The electric power input to the first heat generating element 116 gradually increases after start of input, as indicated with the dashed line of FIG. 5. As a result, the first heat generating element 116 gradually increases. After the temperature of the first heat generating element 116 reaches the target temperature T1, the electric power input to the first heat generating element 116 decreases, because it suffices that the temperature thereof is maintained.

When heating is continued in the first mode, because moisture of the living tissue serving as the treatment target is reduced due to evaporation, the electric power necessary for maintaining the temperature of the first heat generating element 116 gradually decreases. In addition, when the moisture of the living tissue is evaporated, the state of the living tissue becomes stable, and change in electric power necessary for maintaining the temperature of the first heat generating element 116 decreases.

At the time tc, the target temperature of the first heat generating element 116 is switched to the temperature T2. At the time, the electric power input to the first heat generating element 116 increases to increase the temperature of the first heat generating element 116. After the temperature of the first heat generating element 116 reaches the target temperature T2, the electric power input to the first heat generating element 116 decreases, because it suffices that the temperature of the first heat generating element 116 is maintained.

The following is explanation of the condition for determining the timing to switch from the first mode to the second mode. Some conditions may exist.

For example, the mode may be switched from the first mode to the second mode, based on the elapsed time that has passed from the start of input of electric power to the first heat generating element 116 and the second heat generating element 118. Specifically, for example, when a predetermined elapsed time has passed, the mode may be switched from the first mode to the second mode.

In addition, for example, the mode may be switched from the first mode to the second mode, based on the electric power amount input to the first heat generating element 116 or the second heat generating element 118. Specifically, for example, when a predetermined electric power amount has been input to the first heat generating element 116 or the second heat generating element 118 as the integrated amount, the mode may be switched from the first mode to the second mode.

In addition, as described above, when the treatment progresses and the moisture content of the living tissue serving as the treatment target decreases, the electric power necessary for maintaining the temperature of the first heat generating element 116 or the second heat generating element 118 decreases. For this reason, for example, the mode may be switched from the first mode to the second mode, when the electric power input to the first heat generating element 116 or the second heat generating element 118 is reduced to be smaller than a predetermined electric power value.

As described above, when the treatment progresses and the moisture content of the living tissue serving as the treatment target decreases and thereafter becomes stable, the change amount of the electric power necessary for maintaining the temperature of the first heat generating element 116 or the second heat generating element 118 decreases. For this reason, for example, the mode may be switched from the first mode to the second mode, when the change amount of the electric power input to the first heat generating element 116 or the second heat generating element 118 is reduced to be smaller than a predetermined value.

The conditions described above may be properly combined, to determine the timing to switch from the first mode to the second mode.

This explanation explains the example of the case where the temperature of the first heat generating element 116 is set to a relatively high temperature, and the temperature of the second heat generating element 118 is set to a relatively low temperature in the latter period mode, but they may be set conversely as a matter of course. Specifically, the temperature of the first heat generating element 116 may be set to a relatively low temperature, and the temperature of the second heat generating element 118 may be set to a relatively high temperature.

In the example explained in FIG. 5, the target temperature of the second heat generating element 118 is the same in the former period mode and the latter period mode, but the target temperature thereof may be different. Specifically, for example, both the target temperature of the first heat generating element 116 and the target temperature of the second heat generating element 118 in the former period mode may be 200° C., the target temperature of the first heat generating element 116 in the latter period mode may be 300° C., and the target temperature of the second heat generating element 118 in the latter period mode may be 250° C.

Second Example

The second example is also the case where the former period mode is the first mode, and the latter period mode is the second mode. However, specifically, for example, the target temperature of the first heat generating element 116 and the second heat generating element 118 is set to an optimal temperature for incising the living tissue in the former period mode. For example, the optimal temperature for incising the living tissue is within a range of 250° C. to 300° C., preferably 300° C. The present example explains the case where the target temperature of the first heat generating element 116 and the second heat generating element 118 is 300° C. in the former period mode. In the latter period mode, the target temperature of the first heat generating element 116 is set to an optimal temperature for incising the living tissue, and the target temperature of the second heat generating element 118 is set to an optimal temperature for sealing the living tissue. The optimal temperature for sealing the living tissue is within a range of 50° C. to 250° C., preferably 200° C. The present example explains the case where the target temperature of the first heat generating element 116 is 300° C. and the target temperature of the second heat generating element 118 is 200° C.

By setting the first heat generating element 116 and the second heat generating element 118 to 300° C. that is a relatively high temperature, the temperature of the living tissue is increased to a temperature enabling incision. In this manner, prompt incision is enabled in, for example, a region without a problem of bleeding. Thereafter, the temperature of the second heat generating element 118 is reduced to 200° C. that is a relatively low temperature. This configuration prevents carbonization of the living tissue caused by input of excessive energy to the living tissue. In addition, the holding unit 110 can be cooled to a certain degree, by decreasing the temperature of the second heat generating element 118. This configuration prevents damage to another tissue due to contact of the high-temperature holding unit 110 to the tissue, which may occur when the holding unit 110 is moved after treatment. In the latter period mode, electric power input to the second heat generating element 118 may be shut out, to decrease the temperature of the second heat generating element 118 to the environmental temperature.

Figure 6:
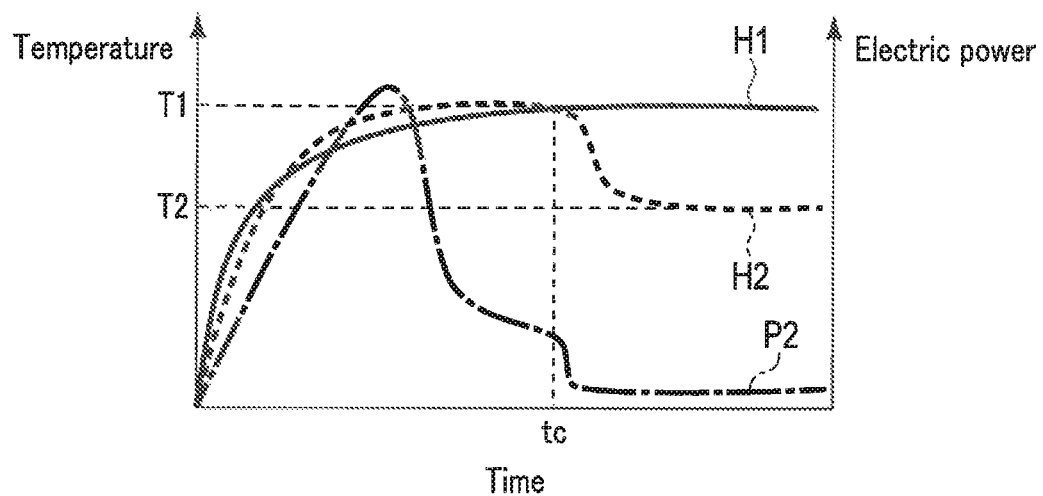
FIG. 6 is a diagram illustrating an example of outlines of the temperature and input power of the heat generating element according to a second example of a combination of the former period mode and the latter period mode.

FIG. 6 shows relation between the temperatures of the first heat generating element 116 and the second heat generating element 118, and the electric power input to the second heat generating element 118, with respect to the time during treatment. In FIG. 6, a solid line H1 indicates the temperature of the first heat generating element 116, a broken line H2 indicates the temperature of the second heat generating element 118, and a dashed line P2 indicates the electric power input to the second heat generating element 118. At time tc, the mode is switched from the first mode to the second mode. The temperature T1 is the target temperature of the first heat generating element 116 and the second heat generating element 118 in the former period mode. The temperature T1 is also the target temperature of the first heat generating element 116 in the latter period mode. The temperature T2 is the target temperature of the second heat generating element 118 in the latter period mode.

As shown in FIG. 6, before the time tc, because the electric power to be supplied to the first heat generating element 116 and the second heat generating element 118 is controlled in the first mode, the temperatures of the first heat generating element 116 and the second heat generating element 118 change in substantially the same manner. The electric power input to the second heat generating element 118 gradually increases after start of input, as indicated with the dashed line of FIG. 6. As a result, the temperature of the second heat generating element 118 gradually increases. After the temperature of the second heat generating element 118 reaches the target temperature T1, the electric power input to the second heat generating element 118 decreases, because it suffices that the temperature thereof is maintained.

At the time tc, the target temperature of the second heat generating element 118 is switched to the temperature T2. At the time, the electric power input to the second heat generating element 118 decreases to decrease the temperature of the second heat generating element 118. After the temperature of the second heat generating element 118 reaches the target temperature T2, the electric power input to the second heat generating element 118 becomes substantially constant as a small value, because it suffices that the temperature of the second heat generating element 118 is maintained.

The following is explanation of the condition for determining the timing to switch from the first mode to the second mode. Although some conditions may exist, they are the same as those in the first example. Specifically, for example, the mode may be switched from the first mode to the second mode, based on the elapsed time that has passed from the start of input of electric power to the first heat generating element 116 and the second heat generating element 118. In addition, for example, the mode may be switched from the first mode to the second mode, based on the electric power amount input to the first heat generating element 116 or the second heat generating element 118. In addition, because the necessary electric power decreases when incision progresses, the mode may be switched from the first mode to the second mode, for example, after the electric power input to the first heat generating element 116 or the second heat generating element 118 becomes smaller than a predetermined electric power value. In addition, because the state becomes stable and change in the necessary electric power decreases when incision progresses, the mode may be switched from the first mode to the second mode, for example, after the change amount of the electric power input to the first heat generating element 116 or the second heat generating element 118 becomes smaller than a predetermined value. In addition, the conditions described above may be properly combined, to determine the timing to switch from the first mode to the second mode.

This example explains the case where the temperature of the first heat generating element 116 is set to a relatively high temperature and the temperature of the second heat generating element 118 is set to a relatively low temperature in the latter period mode, but they may be set conversely as a matter of course. Specifically, the temperature of the first heat generating element 116 may be set to a relatively low temperature, and the temperature of the second heat generating element 118 may be set to a relatively high temperature. In addition, the target temperature of the first heat generating element 116 may be different between the former period mode and the latter period mode.

Third Example

The third example is the case where the former period mode is the second mode in which the target temperature of the first heat generating element 116 is different from the target temperature of the second heat generating element 118, and the latter period mode is the first mode in which the target temperature of the first heat generating element 116 is equal to the target temperature of the second heat generating element 118. More specifically, for example, in the former period mode, the target temperature of the first heat generating element 116 is set to an optimal temperature for incising the living tissue, and the target temperature of the second heat generating element 118 is set to an optimal temperature for sealing the living tissue. The present example explains the case where the target temperature of the first heat generating element 116 is set to 300° C., and the target temperature of the second heat generating element 118 is set to 200° C. In the latter period mode, the target temperature of the first heat generating element 116 and the target temperature of the second heat generating element 118 is set to an optimal temperature for incising the living tissue. In the present example, the target temperature of the first heat generating element 116 and the second heat generating element 118 is set to 300° C.

In the former period mode, the temperature of the first heat generating element 116 is set to a relatively high temperature while the temperature of the second heat generating element 118 is set to a relatively low temperature, to incise the living tissue while the living tissue is coagulated. In the latter period mode, the second heat generating element 118 is also set to the relatively high temperature, to securely incise the living tissue.

In the latter period mode, both the first heat generating element 116 and the second heat generating element 118 are set to a relatively high temperature. This configuration enables secure incision of even a thick tissue or a tough tissue. By contrast, in the former mode, the temperature of the second heat generating element 118 is set to a relatively low temperature, because insufficient coagulation of the living tissue may occur when the second heat generating element 118 is set to a high temperature from the start. Specifically, in the former period mode, incision can be progressed while the living tissue is sufficiently coagulated.

Figure 7:
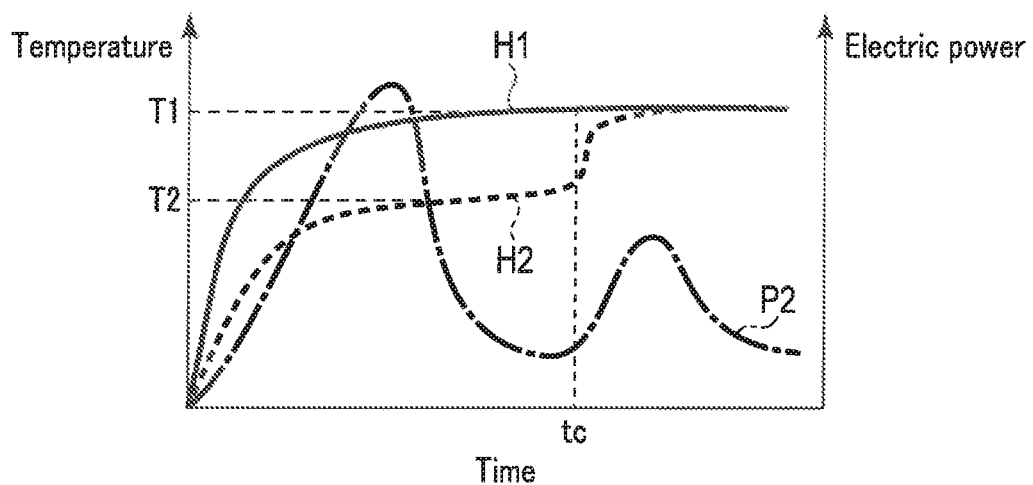
FIG. 7 is a diagram illustrating an example of outlines of the temperature and input power of the heat generating element according to a third example of a combination of the former period mode and the latter period mode.

FIG. 7 shows relation between the temperatures of the first heat generating element 116 and the second heat generating element 118, and the electric power input to the second heat generating element 118, with respect to the time during treatment. In FIG. 7, a solid line H1 indicates the temperature of the first heat generating element 116, a broken line H2 indicates the temperature of the second heat generating element 118, and a dashed line P2 indicates the electric power input to the second heat generating element 118. At time tc, the mode is switched from the second mode to the first mode. The temperature T1 is the target temperature of the first heat generating element 116 in the former period mode. The temperature T1 is also the target temperature of the first heat generating element 116 and the second heat generating element 118 in the latter period mode. The temperature T2 is the target temperature of the second heat generating element 118 in the former period mode.

As shown in FIG. 7, before the time tc, because the electric power to be supplied to the first heat generating element 116 and the second heat generating element 118 is controlled in the second mode, the temperature of the first heat generating element 116 is adjusted to the temperature T1, and the temperature of the second heat generating element 118 is adjusted to the temperature T2. The electric power input to the second heat generating element 118 gradually increases after start of input, as indicated with the dashed line of FIG. 7. As a result, the temperature of the second heat generating element 118 gradually increases. After the temperature of the second heat generating element 118 reaches the target temperature T2, the electric power input to the second heat generating element 118 decreases, because it suffices that the temperature thereof is maintained.

After the time tc, control is performed in the first mode. The target temperature of the second heat generating element 118 is switched to the temperature T1. At the time, the electric power input to the second heat generating element 118 increases to increase the temperature of the second heat generating element 118. After the temperature of the second heat generating element 118 reaches the target temperature T1, the electric power input to the second heat generating element 118 decreases, because it suffices that the temperature of the second heat generating element 118 is maintained.

The following is explanation of the condition for determining the timing to switch from the second mode to the first mode. Although some conditions may exist, they are the same as those in the first example. Specifically, for example, the mode may be switched from the second mode to the first mode, based on the elapsed time that has passed from the start of input of electric power to the first heat generating element 116 and the second heat generating element 118. In addition, for example, the mode may be switched from the second mode to the first mode, based on the electric power amount input to the first heat generating element 116 or the second heat generating element 118. In addition, the mode may be switched from the second mode to the first mode, for example, when the electric power input to the first heat generating element 116 or the second heat generating element 118 becomes smaller than a predetermined electric power value. In addition, the mode may be switched from the second mode to the first mode, for example, when the change amount of the electric power input to the first heat generating element 116 or the second heat generating element 118 becomes smaller than a predetermined value. In addition, the conditions described above may be properly combined, to determine the timing to switch from the second mode to the first mode.

This example explains the case where the temperature of the first heat generating element 116 is set to a relatively high temperature and the temperature of the second heat generating element 118 is set to a relatively low temperature in the former period mode, but they may be set conversely as a matter of course. Specifically, the temperature of the first heat generating element 116 may be set to a relatively low temperature, and the temperature of the second heat generating element 118 may be set to a relatively high temperature. In addition, the target temperature of the first heat generating element 116 may be different between the former period mode and the latter period mode.

Fourth Example

The fourth example is the case where the former period mode is the second mode in which the target temperature of the first heat generating element 116 is different from the target temperature of the second heat generating element 118, and the latter period mode is the first mode in which the target temperature of the first heat generating element 116 is equal to the target temperature of the second heat generating element 118. More specifically, for example, in the former period mode, the target temperature of the first heat generating element 116 is set to an optimal temperature for incising the living tissue, and the target temperature of the second heat generating element 118 is set to an optimal temperature for sealing the living tissue. The present example explains the case where the target temperature of the first heat generating element 116 is set to 300° C., and the target temperature of the second heat generating element 118 is set to 200° C. In the latter period mode, the target temperature is set to an optimal temperature for sealing the living tissue. In the present example, the target temperature of the first heat generating element 116 and the second heat generating element 118 is set to 200° C.

In the former period mode, the temperature of the first heat generating element 116 is set to a relatively high temperature while the temperature of the second heat generating element 118 is set to a relatively low temperature, to incise the living tissue while the living tissue is coagulated. In the latter period mode, the first heat generating element 116 is also set to the relatively low temperature, to prevent carbonization of the living tissue caused by input of excessive energy to the living tissue. In addition, the holding unit 110 can be cooled to a certain degree by decreasing the temperature of the first heat generating element 116. This configuration prevents damage to another tissue due to contact of the high-temperature holding unit 110 to the tissue after treatment.

This example is also effective for the case where treatment of the living tissue is repeated, that is, the case where the former period mode and the latter period mode are repeated to successively treat the living tissue. Specifically, in the latter period mode, because both the first heat generating element 116 and the second heat generating element 118 are maintained at 200° C., the first heat generating element 116 can be promptly set to 300° C. and the second heat generating element 118 can be promptly set to 200° C. in the subsequent treatment in the former period mode.

Figure 8:
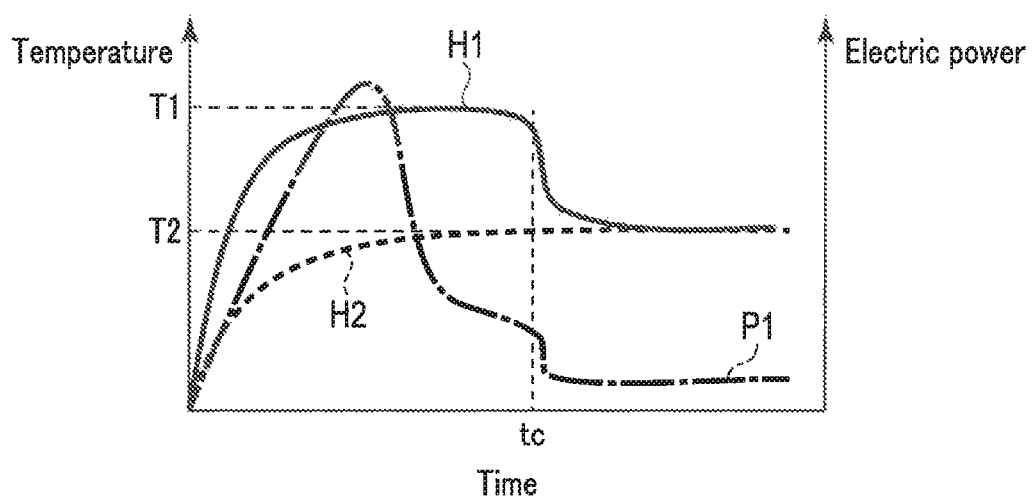
FIG. 8 is a diagram illustrating an example of outlines of the temperature and input power of the heat generating element according to a fourth example of a combination of the former period mode and the latter period mode.

FIG. 8 shows relation between the temperatures of the first heat generating element 116 and the second heat generating element 118, and the electric power input to the first heat generating element 116, with respect to the time during treatment. In FIG. 8, a solid line H1 indicates the temperature of the first heat generating element 116, a broken line H2 indicates the temperature of the second heat generating element 118, and a dashed line P1 indicates the electric power input to the first heat generating element 116. At time tc, the mode is switched from the second mode to the first mode. The temperature T1 is the target temperature of the first heat generating element 116 in the former period mode. The temperature T2 is the target temperature of the second heat generating element 118 in the former period mode. The temperature T2 is also the target temperature of the first heat generating element 116 and the second heat generating element 118 in the latter period mode.

As shown in FIG. 8, before the time tc, because the electric power to be supplied to the first heat generating element 116 and the second heat generating element 118 is controlled in the second mode, the temperature of the first heat generating element 116 is adjusted to the temperature T1, and the temperature of the second heat generating element 118 is adjusted to the temperature T2. The electric power input to the first heat generating element 116 gradually increases after start of input, as indicated with the dashed line of FIG. 8. As a result, the first heat generating element 116 gradually increases. After the temperature of the first heat generating element 116 reaches the target temperature T1, the electric power input to the first heat generating element 116 decreases, because it suffices that the temperature thereof is maintained.

After the time tc, control is performed in the first mode. The target temperature of the first heat generating element 116 is switched to the temperature T2. At the time, the electric power input to the first heat generating element 116 decreases to decrease the temperature of the first heat generating element 116. After the temperature of the first heat generating element 116 reaches the target temperature T2, the electric power input to the first heat generating element 116 decreases, because it suffices that the temperature of the first heat generating element 116 is maintained.

The following is explanation of the condition for determining the timing to switch from the second mode to the first mode. Although some conditions may exist, they are the same as those in the first example. Specifically, for example, the mode may be switched from the second mode to the first mode, based on the elapsed time that has passed from the start of input of electric power to the first heat generating element 116 and the second heat generating element 118. In addition, for example, the mode may be switched from the second mode to the first mode, based on the electric power amount input to the first heat generating element 116 or the second heat generating element 118. In addition, the mode may be switched from the second mode to the first mode, for example, after the electric power input to the first heat generating element 116 or the second heat generating element 118 becomes smaller than a predetermined electric power value, because the necessary electric power to be input to the first heat generating element 116 becomes small when incision is finished. In addition, the mode may be switched from the second mode to the first mode, for example, after the change amount of the electric power input to the first heat generating element 116 or the second heat generating element 118 becomes smaller than a predetermined value, because the electric power to be input to the first heat generating element 116 becomes stable when incision is finished. In addition, the conditions described above may be properly combined, to determine the timing to switch from the second mode to the first mode.

This example explains the case where the temperature of the first heat generating element 116 is set to a relatively high temperature and the temperature of the second heat generating element 118 is set to a relatively low temperature in the former period mode, but they may be set conversely as a matter of course. Specifically, the temperature of the first heat generating element 116 may be set to a relatively low temperature, and the temperature of the second heat generating element 118 may be set to a relatively high temperature. In addition, the target temperature of the second heat generating element 118 may be different between the former period mode and the latter period mode.

Which of the patterns of the first to the fourth examples is used and the target temperatures thereof are set in advance in accordance with the treatment target, the type of treatment, and the type of the device to be used, for example. In addition, the order of the first mode and the second mode, and the set target temperatures are selected in accordance with the coagulation power for the tissue, the incision speed, and the degree of thermal invasion required in the treatment.

As described above, the present embodiment enables switching of the state in which the temperatures of the pair of the first holding member 112 and the second holding member 114 holding the living tissue are set to an equal temperature and the state in which the temperatures of the first holding member 112 and the second holding member 114 are set to different temperatures, during treatment of the living tissue. Consequently, the heating treatment apparatus 1 according to the present embodiment enables optimal treatment in accordance with situations and requirements that are different between treatments, for example, the necessary coagulation power, the incision speed, and the degree of thermal invasion.

<Modifications of Power Supply Unit>

The following is explanation of some modifications relating to the power supply unit 220 of the first embodiment. The difference from the first embodiment will be explained hereinafter, the same parts will be denoted by the same reference characters, and explanation thereof is omitted.

(First Modification)

Figure 9:
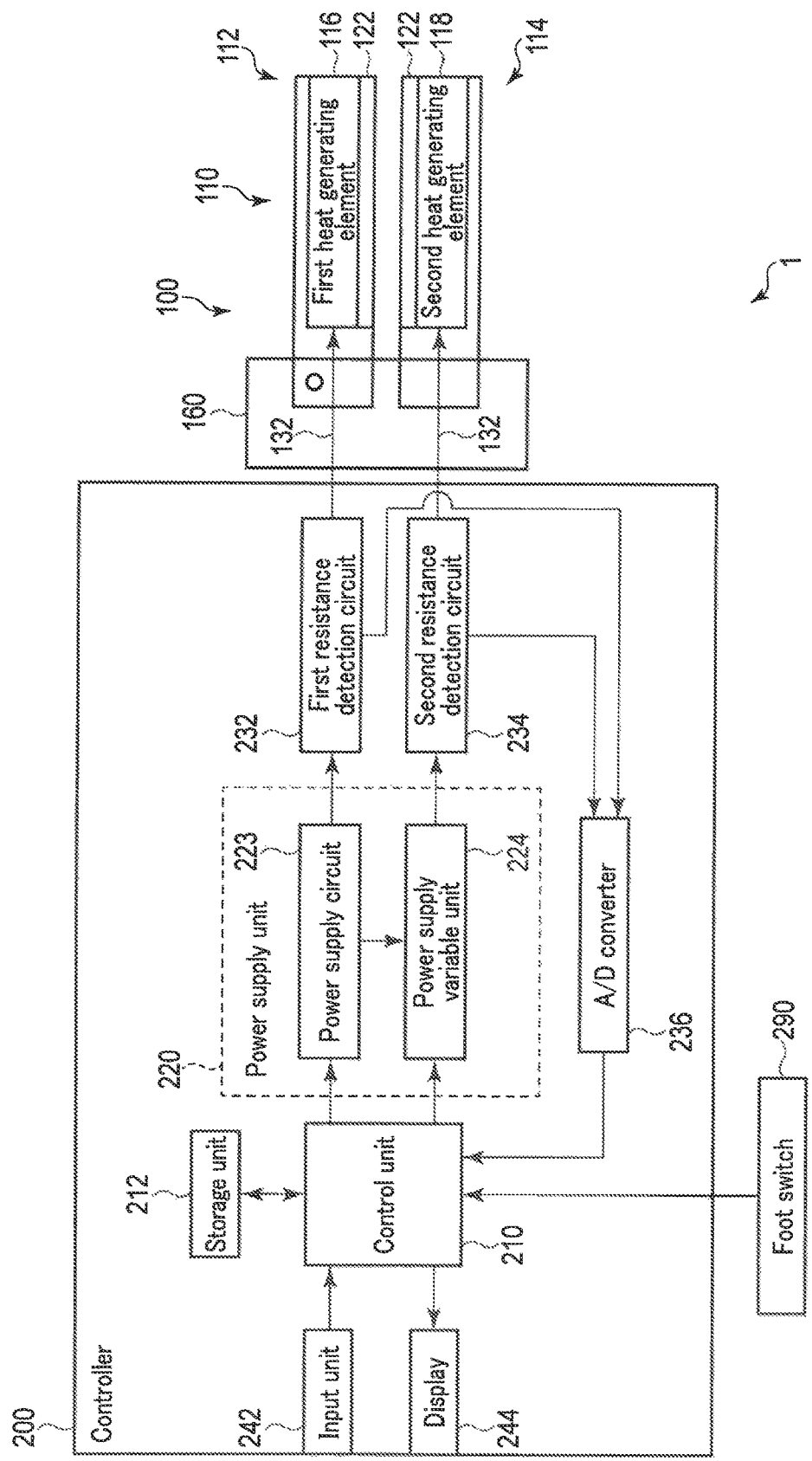
FIG. 9 is a block diagram illustrating a schematic configuration example of a heating treatment apparatus according to a first modification of the first embodiment.

The first modification will be explained hereinafter. The present modification is different from the first embodiment in the structure of the power supply unit 220. FIG. 9 shows a schematic configuration example of the heating treatment apparatus 1 according to the present modification. In the first embodiment, the power supply unit 220 includes two power supply circuits, that is, the first power supply circuit 221 and the second power supply circuit 222. By contrast, the power supply unit 220 according to the present modification includes only one power supply circuit 223. By contrast, the power supply unit 220 includes a power supply variable unit 224 to supply different electric powers to the first heat generating element 116 and the second heat generating element 118.

The first heat generating element 116 is supplied with the electric power output from the power supply circuit 223 as it is through the first resistance detection circuit 232. By contrast, the second heat generating element 118 is supplied with the electric power output from the power supply circuit 223 and regulated in the power supply variable unit 224 through the second resistance detection circuit 234.

The control unit 210 controls the output of the power supply circuit 223, and adjustment of the output with the power supply variable unit 224. For example, the electric power supplied to the first heat generating element 116 is adjusted to be always larger than the electric power supplied to the second heat generating element 118. The output of the power supply circuit 223 is set to a value corresponding to the electric power to be supplied to the first heat generating element 116. The power supply variable unit 224 suppresses the output of the power supply circuit 223, to adjust the output to the electric power to be supplied to the second heat generating element 118.

The present modification simplifies the structure of the power supply unit 220, because the present modification removes the necessity for providing a plurality of power supply circuits.

The following is an example of the power supply variable unit 224. The power supply variable unit 224 includes, for example, a switch. For example, in the upper part of FIG. 10, a solid line H1 indicates the temperature of the first heat generating element 116 with respect to the time, and a broken line H2 indicates the temperature of the second heat generating element 118 with respect to the time. As shown in the upper part of FIG. 10, it is supposed that the target temperature of the first heat generating element 116 is the temperature T1, and the target temperature of the second heat generating element 118 is the temperature T2. The temperature T2 is lower than the temperature T1.

Figure 10:
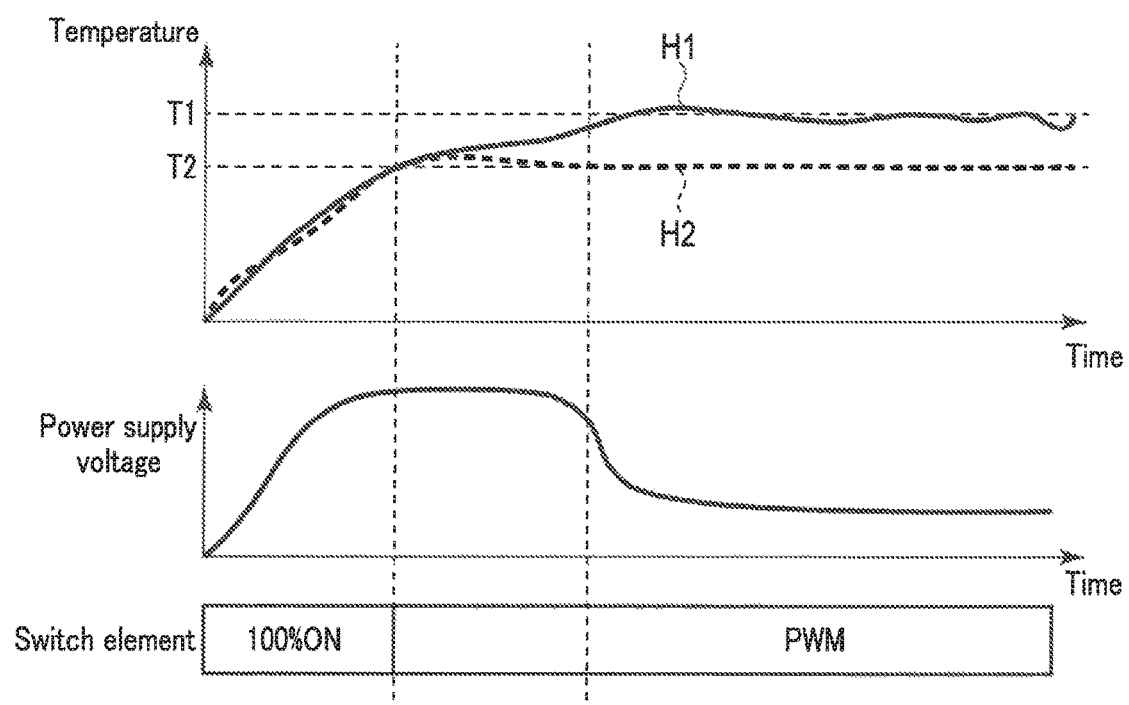
FIG. 10 is a diagram for explaining an example of operations of a power supply unit according to the first modification of the first embodiment.

When the temperatures of the first heat generating element 116 and the second heat generating element 118 are lower than the target temperature T1, the output voltage of the power supply circuit 223 is adjusted in accordance with the temperature of the first heat generating element 116, as shown in the middle part of FIG. 10. The output voltage in this state is relatively high. In this state, as shown in the lower part of FIG. 10, the switch of the power supply variable unit 224 is continuously turned on.

When the temperature of the second heat generating element 118 reaches the target temperature T2 but the temperature of the first heat generating element 116 does not reach the target temperature T1, the output voltage of the power supply circuit 223 is still relatively high, to increase the temperature of the first heat generating element 116. When application of the voltage is continued, the temperature of the second heat generating element 118 becomes higher than the temperature T2. For this reason, the switch of the power supply variable unit 224 is turned on and off repeatedly to maintain the temperature of the second heat generating element 118 at the target temperature T2, as shown in the lower part of FIG. 10. Specifically, the electric power supplied to the second heat generating element 118 is adjusted by Pulse Width Modulation (PWM).

After the temperature of the first heat generating element 116 reaches the target temperature T1, the voltage applied to the first heat generating element 116 decreases, to maintain the temperature. Specifically, the output voltage of the power supply circuit 223 decreases. Because the voltage to be applied to the second heat generating element 118 is further lower than the voltage applied to the first heat generating element 116, the power supply variable unit 224 performs adjustment by PWM using the output of the power supply circuit 223.

As described above, the power supply variable unit 224 including the switch is capable of adjusting the output of the power supply circuit 223 to a proper value by PWM, in accordance with the electric power amount supplied to the second heat generating element 118.

The power supply variable unit 224 may include a variable resistor, instead of the switch. The power supply variable unit 224 may adjust the output voltage of the power supply circuit 223 with the variable resistance, to adjust the electric power supplied to the second heat generating element 118 to a proper value.

The power supply variable unit 224 may include a variable gain amplifier. The power supply variable unit 224 may adjust the output of the power supply circuit 223 with the variable gain amplifier, to a proper value as the electric power supplied to the second heat generating element 118.

(Second Modification)

Figure 11:
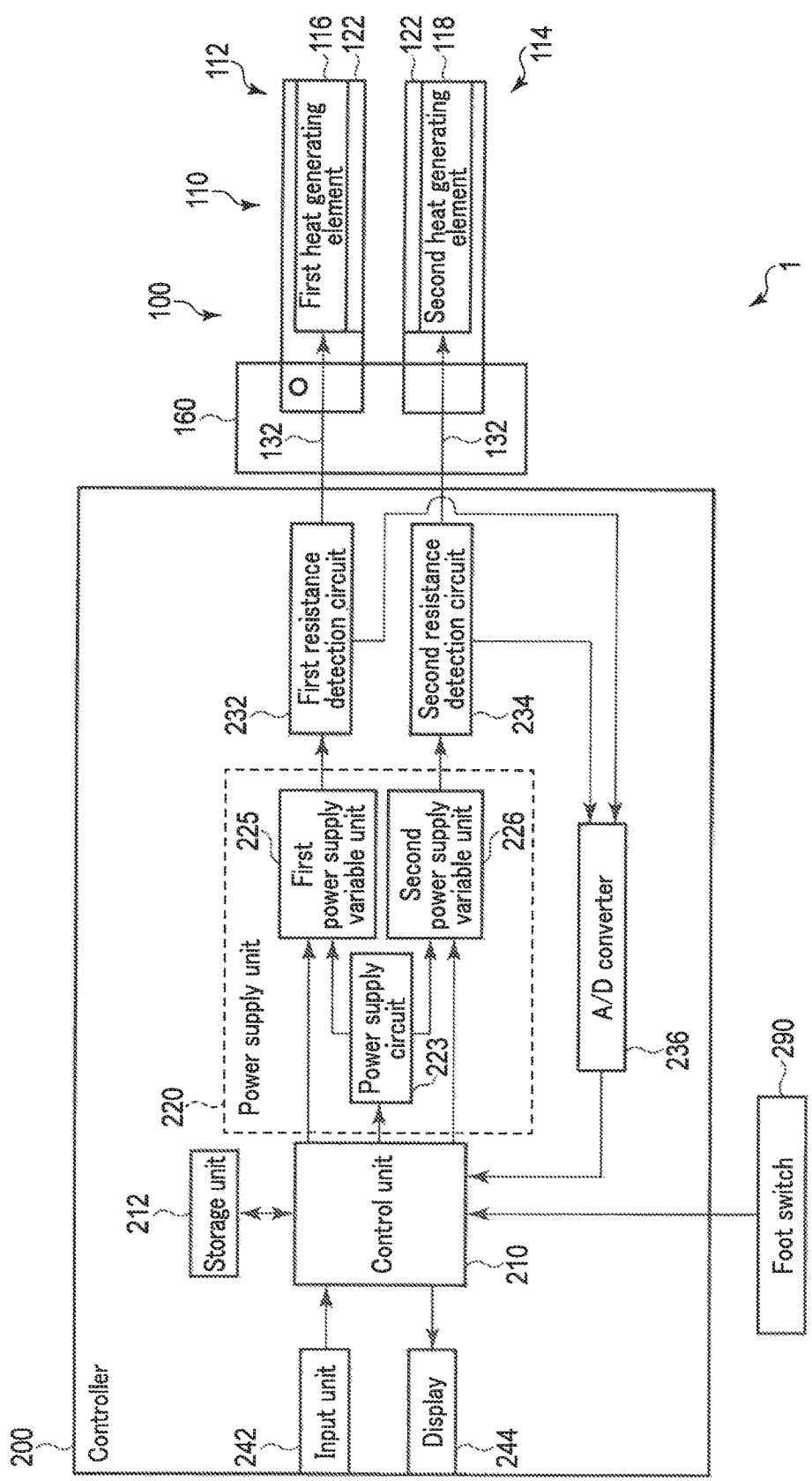
FIG. 11 is a block diagram illustrating a schematic configuration example of a heating treatment apparatus according to a second modification of the first embodiment.

The second modification will be explained hereinafter. In the present modification, two power supply variable units are provided. FIG. 11 shows a schematic configuration example of the heating treatment apparatus 1 according to the present modification. In the present modification, a first power supply variable unit 225 is provided between the power supply circuit 223 and the first resistance detection circuit 232, and a second power supply variable unit 226 is provided between the power supply circuit 223 and the second resistance detection circuit 234. Specifically, the first heat generating element 116 is supplied with electric power through the first power supply variable unit 225. The second heat generating element 118 is supplied with electric power through the second power supply variable unit 226.

Each of the first power supply variable unit 225 and the second power supply variable unit 226 may include a switch, a variable resistor, or a variable gain amplifier, in the same manner as the first modification.

Providing the first power supply variable unit 225 and the second power supply variable unit 226 enables setting either of the electric power supplied to the first heat generating element 116 and the electric power supplied to the second heat generating element 118 to be larger than the other. Specifically, this structure improves the flexibility in control of electric power supply to the first heat generating element 116 and the second heat generating element 118.

Figure 12:
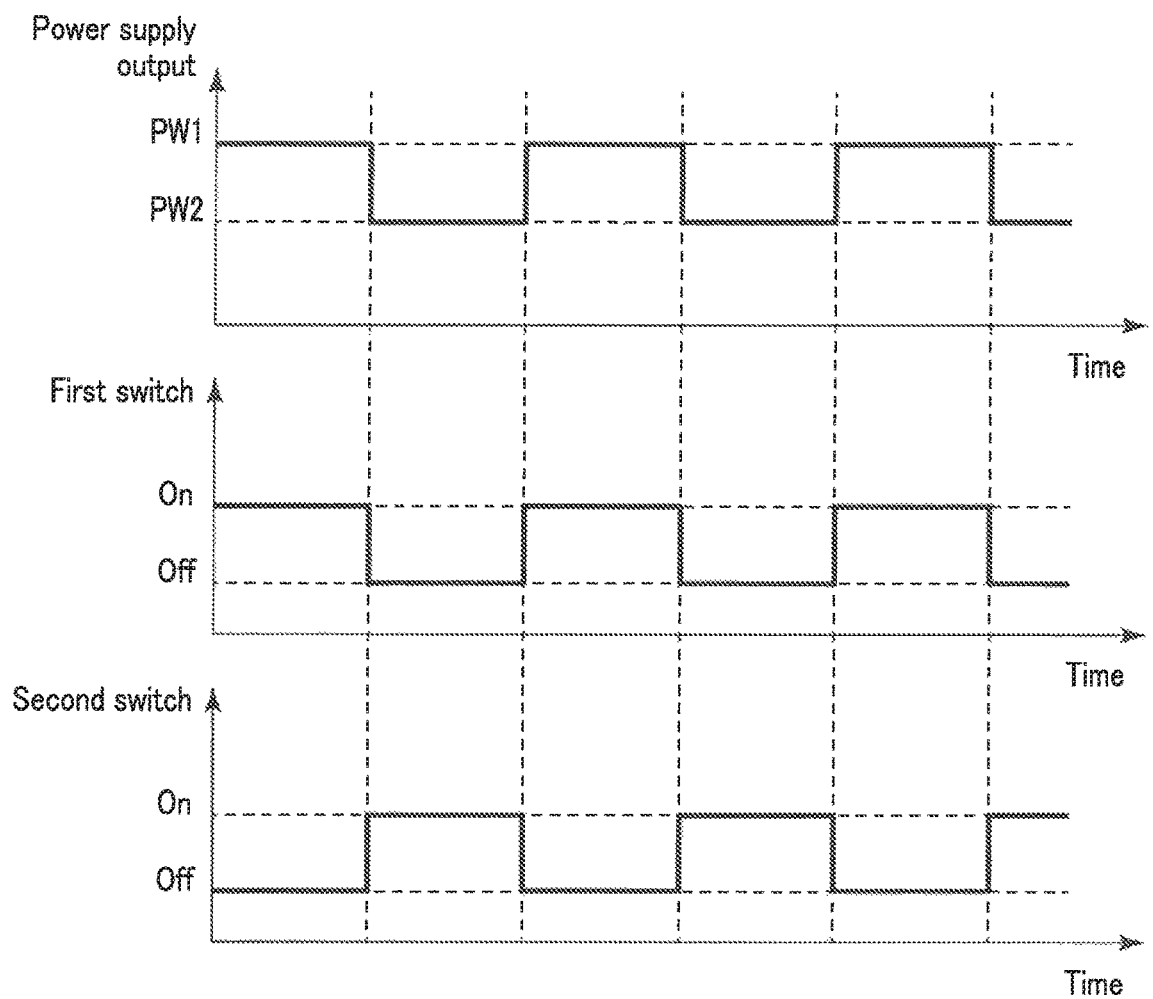
FIG. 12 is a diagram for explaining an example of operations of a power supply unit according to the second modification of the first embodiment.

The following is explanation of an example of operations of the power supply unit 220 in the case where each of the first power supply variable unit 225 and the second power supply variable unit 226 includes a switch, with reference to FIG. 12. The upper part of FIG. 12 shows the output of the power supply circuit 223 with respect to the elapsed time, the middle part of FIG. 12 shows the turning on/off state of the switch included in the first power supply variable unit 225, and the lower part of FIG. 12 shows the turning on/off state of the switch included in the second power supply variable unit 226.

In the case shown in FIG. 12, supplying electric power PW1 to the first heat generating element 116 and supplying electric power PW2 to the second heat generating element 118 are repeated. Specifically, the output of the power supply circuit 223 is alternately switched between PW1 and PW2. When the output of the power supply circuit 223 is PW1, the first switch (SW) of the first power supply variable unit 225 is turned on, and the second switch (SW) of the second power supply variable unit 226 is turned off. By contrast, when the output of the power supply circuit 223 is PW2, the second switch of the second power supply variable unit 226 is turned on, and the first switch of the first power supply variable unit 225 is turned off.

As described above, supplies of electric power to the first heat generating element 116 and the second heat generating element 118 are performed alternately, not simultaneously, and thereby load on the power supply circuit 223 is reduced.

Second Embodiment

The following is explanation of the second embodiment. The difference of the second embodiment from the first embodiment will be explained hereinafter, the same parts thereof are denoted with the same reference characters, and explanation thereof is omitted. The heating treatment apparatus 1 according to the present embodiment has a function of a high-frequency treatment tool, in addition to the heating treatment apparatus 1 of the first embodiment.

FIG. 13 shows a schematic configuration example of the heating treatment apparatus 1 according to the present embodiment. The controller 200 according to the present embodiment includes a third power supply circuit 252, and an impedance detection unit 254, in addition to the configuration in the case of the first embodiment. The third power supply circuit 252 is connected with the control unit 210. The third power supply circuit 252 outputs a high-frequency voltage under the control of the control unit 210. The high-frequency voltage output from the third power supply circuit 252 is applied between the heat transfer member 122 having electric conductivity of the first holding member 112 and the heat transfer member 122 having electric conductivity of the second holding member 114. Accordingly, a high-frequency voltage is applied to the living tissue held between the first holding member 112 and the second holding member 114. As a result, a high-frequency current flows through the living tissue, and the living tissue generates heat. The living tissue is coagulated with the generated heat. In the present embodiment, the living tissue is treated using heat generated with the high-frequency current flowing through the living tissue, in addition to the heat generated with the first heat generating element 116 and the second heat generating element 118.

The impedance detection unit 254 is inserted between the third power supply circuit 252 and the heat transfer members 122 of the first holding member 112 and the second holding member 114. The impedance detection unit 254 acquires impedance relating to the circuit starting from the third power supply circuit 252 and returning to the third power supply circuit 252 through the heat transfer member 122 of the first holding member 112, the living tissue, and the heat transfer member 122 of the second holding member 114. The impedance detection unit 254 transmits the acquired information of impedance to the control unit 210 via the A/D converter 236. The impedance acquired by the impedance detection unit 254 properly indicates the state of the living tissue and the contact state between the heat transfer member 122 and the living tissue.

Figure 14:
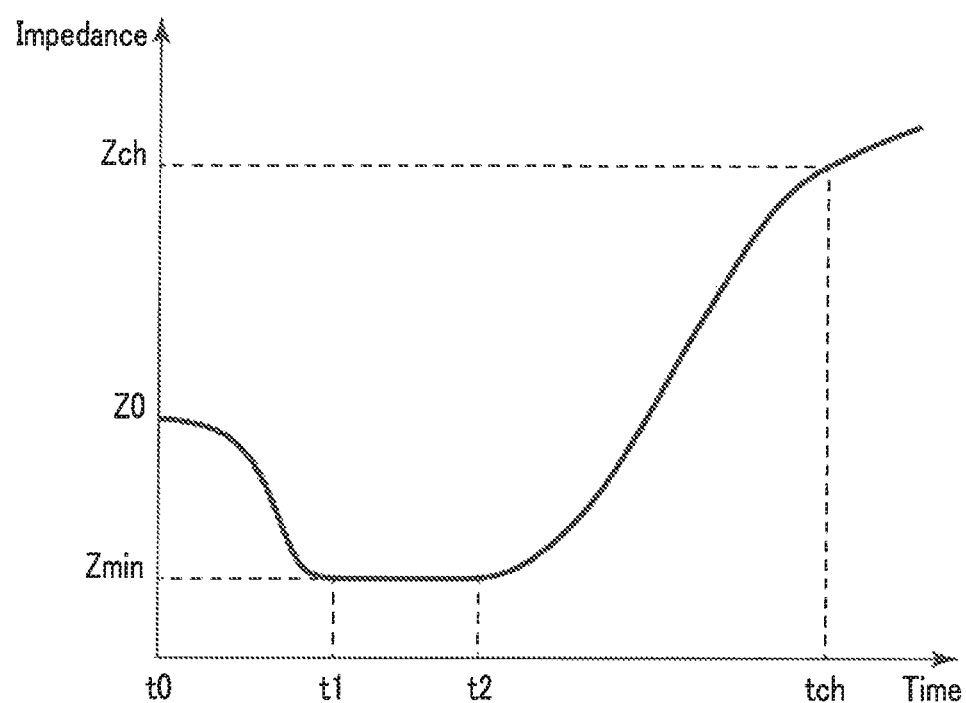
FIG. 14 is a diagram for explaining an example of an outline of change in impedance for the time in treatment.

In the present embodiment, the control unit 210 determines the timing to switch from the former period mode to the latter period mode, based on the information of the impedance acquired by the impedance detection unit 254. FIG. 14 shows an outline of an example of change in impedance with respect to the time. The impedance at the treatment start time t0 is referred to as initial impedance Z0. Because the moisture of the living tissue is evaporated right after start of treatment, the impedance gradually decreases from the initial impedance Z0. Thereafter, the impedance indicates a substantially constant value. The impedance in this state is referred to as low impedance Zmin. The time from time t1 to time t2 indicating the low impedance Zmin is referred to as low impedance continuance time. After the time t2, the living tissue is gradually coagulated, and the impedance in this state gradually increases. When the predetermined conditions are satisfied, the mode is switched from the former period mode to the latter period mode. This timing to switch the mode is referred to as switching timing tch, and the impedance at the timing tch is referred to as switching impedance Zch.

Some conditions exist as conditions for switching from the former period mode to the latter period mode. For example, the impedance indicates the state of the tissue. For this reason, after the low impedance Zmin is indicated, the timing at which the impedance increases and reaches a predetermined threshold may be set as the timing to switch the mode. Specifically, the switching impedance Zch may be determined in advance.

In addition, the initial impedance Z0 indicates the size and the moisture content of the tissue or the like. For this reason, the timing at which a predetermined time determined in accordance with the initial impedance Z0 has passed may be set as the timing to switch the mode. Specifically, the switching time tch may be determined based on the initial impedance Z0. As another example, the timing at which the impedance reaches a predetermined threshold determined in accordance with the initial impedance Z0 may be set as the switching timing. Specifically, the switching impedance Zch may be determined based on the initial impedance Z0.

The low impedance continuance time also indicates the size and the moisture content of the tissue or the like. For this reason, the timing at which a predetermined time determined in accordance with the low impedance continuance time has passed from the start of treatment may be set as the switching timing. As another example, the timing at which the impedance reaches a predetermined threshold determined in accordance with the low impedance continuance time may be set as the switching timing.

As another example, the timing at which a predetermined time has passed after the impedance indicates the minimum value may be set as the switching timing.

During treatment, the phases of the voltage and the current change. For this reason, the timing at which phase differences of the voltage and the current reaches a predetermined threshold may be set as the switching timing. As another example, the timing at which changes amount of phase differences of the voltage and the current reaches a predetermined threshold may be set as the switching timing.

In any case, the combination of the former period mode and the latter period mode may be any of the first example to the fourth example explained in the first embodiment. In addition, the structure of the power supply unit 220 may be any of the modifications explained in the first modification.

Determining the timing based on the measured impedance as in the present embodiment enables determination of switching timing in accordance with the living tissue serving as the treatment target. This configuration enables more proper execution of treatment.

This explanation explains the example in which the living tissue is treated also with the high-frequency electric power. The electric power applied to the living tissue may be one of a fixed value, or one changing according to circumstances using, for example, a feedback control system. Application of the high-frequency electric power to the living tissue may be performed only to acquire information relating to the state of the living tissue, not to perform treatment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A heating treatment apparatus to treat a living tissue by heating the living tissue, comprising:
   a first holding plate;
   a second holding plate configured to hold the living tissue together with the first holding plate, and provided to be opposed to the first holding plate;
   a first heat generating element provided on the first holding plate and configured to heat the first holding plate to heat the living tissue;
   a second heat generating element provided on the second holding plate and configured to heat the second holding plate to heat the living tissue;
   a power supply unit configured to supply electric power to cause the first heat generating element and the second heat generating element to generate heat;
   a memory configured to store a condition for mode switching based on a threshold value of the electric power; and
   a control unit configured to:
     control the power supply unit to operate in a first mode such that a temperature of the first heat generating element is the same as a temperature of the second heat generating element,
     detect if the electric power reaches the threshold value by reading the condition for mode switching from the memory, and
     when the electric power reaches the threshold value, control the power supply unit to operate in a second mode such that the temperature of the first heat generating element is different from the temperature of the second heat generating element, the temperature of the first heat generating element and the temperature of the second heat generating element both being nonzero in the second mode.

2. The heating treatment apparatus according to claim 1, wherein the control unit is configured to switch from the first mode to the second mode during treatment of the living tissue.

3. The heating treatment apparatus according to claim 2, wherein, in the second mode, the control unit is configured to increase the temperature of at least one of the first heat generating element or the second heat generating element to be higher than the temperature in the first mode.

4. The heating treatment apparatus according to claim 3,
wherein, in the first mode, the control unit is configured to control the power supply unit to operate such that the temperature of the first heat generating element and the temperature of the second heat generating element are a first optimal temperature for sealing the living tissue, and
wherein, in the second mode, the control unit is configured to control the power supply unit to operate such that the temperature of the first heat generating element is a second optimal temperature for incising the living tissue and the temperature of the second heat generating element is the first optimal temperature for sealing the living tissue.

5. The heating treatment apparatus according to claim 2, wherein, in
the second mode, the control unit is configured to decrease the temperature of at least one of the first heat generating element or the second heat generating element to be lower than the temperature in the first mode.

6. The heating treatment apparatus according to claim 5,
wherein, in the first mode, the control unit is configured to control the power supply unit to operate such that the temperature of the first heat generating element and the temperature of the second heat generating element are a second optimal temperature for incising the living tissue, and
wherein, in the second mode, the control unit is configured to control the power supply unit to operate such that the temperature of the first heat generating element is the second optimal temperature for incising the living tissue and the temperature of the second heat generating element is a first optimal temperature for sealing the living tissue.

7. The heating treatment apparatus according to claim 1, wherein the control unit is configured to switch from the second mode to the first mode during treatment of the living tissue.

8. The heating treatment apparatus according to claim 7, wherein, in the first mode, the control unit is configured to increase the temperature of at least one of the first heat generating element or the second heat generating element to be higher than the temperature in the second mode.

9. The heating treatment apparatus according to claim 8,
wherein, in the second mode, the control unit is configured to control the power supply unit to operate such that the temperature of the first heat generating element is a second optimal temperature for incising the living tissue and the temperature of the second heat generating element is a first optimal temperature for sealing the living tissue, and
wherein, in the first mode, the control unit is configured to control the power supply unit to operate such that the temperature of the first heat generating element and the temperature of the second heat generating element are the second optimal temperature for incising the living tissue.

10. The heating treatment apparatus according to claim 7, wherein, in the first mode, the control unit is configured to decrease the temperature of at least one of the first heat generating element or the second heat generating element to be lower than the temperature in the second mode.

11. The heating treatment apparatus according to claim 10,
wherein, in the second mode, the control unit is configured to control the power supply unit to operate such that the temperature of the first heat generating element is a second optimal temperature for incising the living tissue and the temperature of the second heat generating element is a first optimal temperature for sealing the living tissue, and
wherein, in the first mode, the control unit is configured to control the power supply unit to operate such that the temperature of the first heat generating element and the temperature of the second heat generating element are the first optimal temperature for sealing the living tissue.

12. The heat treatment apparatus according to claim 1, wherein:
the power supply unit comprises a power supply circuit and a power supply variable unit, and
the power supply unit is configured to supply different amounts of electric power to the first heat generating element and the second heat generating element.

13. The heat treatment apparatus according to claim 12, wherein the power supply variable unit is configured to adjust output of electric power by pulse-width modulation.

14. The heat treatment apparatus according to claim 1, wherein the power supply unit comprises a power supply circuit and two power supply variable units.

15. The heat treatment apparatus according to claim 14, wherein the two power supply variable units are alternately turned on.

16. The heat treatment apparatus according to claim 1, further comprising
an impedance detection unit configured to measure impedance of the living tissue to be treated, wherein the control unit is configured to switch between the first mode and the second mode based on a value of the impedance.

17. A controller of a heating treatment apparatus to perform treatment by holding and heating a living tissue with a first holding plate provided with a first heat generating element and a second holding plate provided with a second heat generating element, the second holding plate provided to be opposed to the first holding plate, the controller comprising:
a power supply unit configured to supply electric power to cause the first heat generating element and the second heat generating element to generate heat;
a memory configured to store a condition for mode switching based on a threshold value of the electric power; and
a control unit configured to:
control the power supply unit to operate in a first mode such that a temperature of the first heat generating element is the same as a temperature of the second heat generating element,
detect if the electric power reaches the threshold value by reading the condition for mode switching from the memory, and when the electric power reaches the threshold value, control the power supply unit to operate in a second mode such that the temperature of the first heat generating element is different from the temperature of the second heat generating element, the temperature of the first heat generating element and the temperature of the second heat generating element both being nonzero in the second mode.

18. The controller according to claim 17,
wherein, in the first mode, the control unit is configured to control the power supply unit to operate such that the temperature of the first heat generating element and the temperature of the second heat generating element are a first optimal temperature for sealing the living tissue, and
wherein, in the second mode, the control unit is configured to control the power supply unit to operate such that the temperature of the first heat generating element is a second optimal temperature for incising the living tissue and the temperature of the second heat generating element is the first optimal temperature for sealing the living tissue.

19. The controller according to claim 17,
wherein, in the first mode, the control unit is configured to control the power supply unit to operate such that the temperature of the first heat generating element and the temperature of the second heat generating element are a second optimal temperature for incising the living tissue, and
wherein, in the second mode, the control unit is configured to control the power supply unit to operate such that the temperature of the first heat generating element is the second optimal temperature for incising the living tissue and the temperature of the second heat generating element is a first optimal temperature for sealing the living tissue.

20. The controller according to claim 17,
wherein, in the second mode, the control unit is configured to control the power supply unit to operate such that the temperature of the first heat generating element is a second optimal temperature for incising the living tissue and the temperature of the second heat generating element is a first optimal temperature for sealing the living tissue, and
wherein, in the first mode, the control unit is configured to control the power supply unit to operate such that the temperature of the first heat generating element and the temperature of the second heat generating element are the second optimal temperature for incising the living tissue.

21. The controller according to claim 17,
wherein, in the second mode, the control unit is configured to control the power supply unit to operate such that the temperature of the first heat generating element is a second optimal temperature for incising the living tissue and the temperature of the second heat generating element is a first optimal temperature for sealing the living tissue, and
wherein, in the first mode, the control unit is configured to control the power supply unit to operate such that the temperature of the first heat generating element and the temperature of the second heat generating element are the first optimal temperature for sealing the living tissue.

* * * * *